United States Patent [19]
Urich et al.

[11] Patent Number: 6,155,975
[45] Date of Patent: Dec. 5, 2000

[54] PHACOEMULSIFICATION APPARATUS WITH PERSONAL COMPUTER

[76] Inventors: Alex Urich, 27402 Via Caudaloso, Mission Viejo, Calif. 92692; Michael Curtis, 26421 Pebble Creek, Lake Forest, Calif. 92630; Greg Peña, 910 E. Vine Ave., West Covina, Calif. 91790; Brent Martinez, 11928 Reichling La., Whittier, Calif. 90606

[21] Appl. No.: 09/187,347

[22] Filed: Nov. 6, 1998

[51] Int. Cl.$^7$ ................................................. A61B 5/00
[52] U.S. Cl. ................................ 600/300; 606/34; 607/96
[58] Field of Search ............................. 600/300; 606/32, 606/34, 41, 45, 49; 607/99, 105, 113, 100, 96; 351/239

[56] References Cited

U.S. PATENT DOCUMENTS 5,852,489   12/1998   Chen ........................................ 351/237
5,871,481    2/1999   Kannenberg et al. ..................... 606/34
5,910,139    6/1999   Cochran et al. ............................ 606/1

*Primary Examiner*—Cary O'Connor
*Assistant Examiner*—Ryan Carter
*Attorney, Agent, or Firm*—Law Offices of William L. Klima, P.L.C.

[57] ABSTRACT

A phacoemulsification apparatus including a personal computer for displaying, storing and transmitting data relating to a surgical operation. Preferably, the personal computer is operated by MICROSOFT WINDOWS 95 or 98 software to take advantage of various communication applications.

12 Claims, 6 Drawing Sheets

PHACOEMULSIFICATION APPARATUS WITH PERSONAL COMPUTER

FIELD OF THE INVENTION

A phacoemulsification apparatus including a personal computer for displaying, recording, and transmitting surgical data parameters and audio/video information regarding a particular surgery, and methods of operating the phacoemulsification apparatus and methods of surgery. A preferred embodiment utilizes a personal computer operating on WINDOWS 95 and WINDOWS 98 software.

BACKGROUND OF THE INVENTION

There exists many surgical instruments and apparatus for conducting surgical procedures on animals and humans. Many of these instruments are electrical surgical instruments and include various electrical devices for powering and controlling the surgical instruments.

Currently, most electrical surgical instruments are custom configured and designed for one or more particular surgical applications. These surgical instruments utilize analog and/or digital sensing and control equipment and devices. The outputs from these sensors and controls can be visually displayed on a monitor associated with the electrical surgical instrument.

The information displayed is based on custom software developed with the operating system of the electrical surgical instrument. An instrument designer and/or programmer develops the particular custom hardware and software configurations for displaying the desired information.

In the past, it is believed that electrical surgical apparatus have not been interfaced with a personal computer being operated by WINDOWS 95 and WINDOWS 98 software. The present invention is designed and configured to make the personal computer interface highly reliable and dependable, and suitable for use in controlling an electrical surgical apparatus.

SUMMARY OF THE INVENTION

An object of the present invention is to provide an improved electrical surgical apparatus.

A second object of the present invention is to provide an electrical surgical apparatus including a personal computer.

A third object of the present invention is to provide an electrical surgical apparatus including a personal computer operated by WINDOWS 95 and/or WINDOWS 98 software.

A fourth object of the present invention is to provide an electrical surgical apparatus including a personal computer for displaying and recording information relating to the surgery.

A fifth object of the present invention is to provide an electrical surgical apparatus including a personal computer and a highly reliable and dependable personal computer interface.

A sixth object of the present invention is to provide an electrical surgical apparatus including a personal computer configured for transmitting information relating to the surgery via telephone or internet systems.

A seventh object of the present invention is to provide an electrical surgical apparatus including an electrical surgical device acting as a master and a personal computer acting as a slave.

An eighth object of the present invention is to provide an improved phacoemulsification apparatus.

A ninth object of the present invention is to provide a phacoemulsification apparatus including a personal computer.

A tenth object of the present invention is to provide a phacoemulsification apparatus including a personal computer operated by WINDOWS 95 and/or WINDOWS 98 software.

The present invention relates to electrical surgical apparatus. The electrical surgical apparatus utilizes electrical energy or power for operating one or more functions of the apparatus. Typically, the apparatus would be connected via a power cord to a conventional power source (e.g. 110–115 volt, 15 amp ac wall outlet), or a non-conventional power source with additional power converting equipment.

The present invention particularly relates to electrical surgical apparatus configured to include 1) a control console; 2) separate surgical hand piece electrically connected (e.g. via cable or wire) to the control console; and 3) personal computer.

The control console will typically include a power source (e.g. power cord), power supply for powering the control console circuitry and hand piece, control circuit board(s), driver circuit board(s) for powering the hand piece, and other electrical equipment and devices for controlling and operating the separate surgical hand piece. The control console can be a separate stand alone unit, or can be integrated with the personal computer into a signal cabinet or case. A preferred configuration is with a movable stand supporting the console, and a movable arm supporting the personal computer with a display above the control console.

The surgical hand piece can include an electrical motor, transducer, ultrasonic transducer, magnetostrictive transducer, cooler, heater, electromagnetic generator, cauterizer, cutter, grinder, milling device, drill, laser, light source, and/or other suitable electrical components to conduct various surgical operations. A specific example is a hand piece for a phacoemulsification apparatus for conducting eye surgery for removal of the natural lens of an eye. The hand piece can use a needle driven by an ultrasonic or magnetostrictive transducer, or alternatively, a needle or probe provided with a high speed cutting bit for breaking the natural lens into tiny pieces to be removed through a small incision (e.g. by fluid irrigation and vacuum removal).

The personal computer utilized in the present invention is preferably an IBM compatible DOS based personal computer, WINDOWS 95 and/or WINDOWS 98 based personal computer, or MACINTOSH personal computer, since the current software is user friendly, and there exists substantial software applications for these computer systems. Most preferably, the personal computer is loaded and operated with Microsoft WINDOWS 95 and WINDOWS 98 software.

The personal computer is electrically connected to the console via an electrical cable connected to an isolated serial port of the personal computer. The electrical surgical apparatus is configured to send surgical parameters data from the console to the personal computer via the electrical cable connect to the isolated serial port of the personal computer. Further, the electrical surgical apparatus is configured so that the console acts as a master and the personal computer acts as a slave. If the personal computer experiences a crash, the operation of the control console is not affected.

In the application of the present invention to a phacoemulsification apparatus, the surgical parameters data communicated from the console to the personal computer, for example, may include ultrsnic power level of hand piece, pressure and/or flow within the infusion line, vacuum and/or flow within the aspiration line, flow within the liquid bypass line, peristaltic pump speed, phaco sleeve temperature, diathermy power, footswitch position, mode of operation, mode(s) of information display, modes of data storage and transmission, etc.

The personal computer interface provides the following functions, including:

1) collecting surgical parameters data in real time during the surgical procedure;
2) displaying a menu similar to the menu displayed by the control console such that different functions can be selected either by using a personal computer mouse, keyboard, touch screen, or the control console;
3) displaying the surgical parameters data as continuous graphs as a function of time;
4) storing the surgical parameters data in a data base file;
5) capturing a video signal from a camera placed on the surgical microscope and displaying the picture of the eye undergoing the surgical procedure;
6) storing the picture on a recordable compact disc (CD) as a function of time;
7) Storing the picture on hard disc transferable to a recordal compact disc (CD) as a function of time; and
8) Provide instant replay of the entire or portions of the recorded data parameters and/or video record.
9) Instant replay of record information beginning at any time point in recorded data and/or video.

When visualizing a surgical procedure, the personal computer will associate the name of the file from the compact disc with the name of the file in the data base. Both files are then synchronized in time and displayed in separate windows. Other pertinent data can be computed from the surgical parameters and displayed such as the temperature of the ultrasonic tip which is a function of the ultrasonic power, aspirated flow and incision leak.

A Remote/Phaco Interaction

The Remote Computer implements a novel way to control, monitor and extend the functionality of the Phaco instrument. The Remote replicates the front panel of the Phaco within a standard Windows based program. The application faithfully mirrors the LCD display of the Phaco, and provides buttons that correspond to all the controls on the keypad of the Phaco. The Remote extends the capabilities of the Phaco by providing real-time graphical display of the surgical parameters and measurements, disk storage of the data captured, capture and storage of video data, data entry of patient demographic data, and a database to control access to all patient records.

The Remote and the Phaco communicate via a software protocol transmitted on a serial link. The protocol allows the Phaco to transmit the contents of its LCD display, its program state (mode) and the real-time measurements of the U/S power, vacuum and flow rate. Changes to the LCD display on the Phaco are transmitted simultaneously to the Remote. In addition, the whole contents of the LCD are transmitted every 5 seconds. This ensures that the Remotes' LCD replica will match the Phaco when the Remote is first started. The real-time measurement values, along with a variable representing the current Phaco state are transmitted every 0.25 second. This data is displayed numerically and graphically on the Remote, and stored for later review.

The protocol allows the Remote to transmit virtual keypresses. This design ensures that the Remote has no special control over the operation of the Phaco: it can only stimulate the pressing of a keypad button. All the normal validity checks and range checking that the Phaco ordinarily performs when monitoring its own keypad are activated for all Remote requests. This design also allows for software changes on the Phaco without impacting the Remote program.

Another extension provided by the Remote/Phaco interaction is the ability to add virtual keys to the Phaco system. For example, the Phaco implements an extensive diagnostic function that carefully monitors the priming cycle. This function is initiated by the reception of a keypress from the Remote. The real-time data collected during the diagnostic session is transmitted in a dedicated packet that is stored by the Remote for later review.

All communication between the two machines relies on a serial protocol that ensures the faithful transmission of packets of data in either direction. The packets contain:

a start character
a type code
a length field (for the variable length LCD packets)
the data itself
a checksum The receiving program only parses and acts upon packets whose checksum and start character are correct.

The Phaco only accepts one packet type: a keycode packet. The key code is fed to the low-level keypad monitoring routine. A keycode packet transmission involves two steps:

a keycode packet is transmitted when a button is first pressed on the Remote window
a second packet is sent when the key is released.

This two-packet pattern replicates the keypad hardware on the Phaco, and allows the auto-repeat function (holding a key pressed) to work the same regardless of source (either Phaco or Remote).

The Remote accepts LCD packets that contain the location and contents of a string of characters. These packets may specify a single text character, or a complete LCD line of 40 characters.

The Remote accepts LCD packets that contain the location and contents of a string of characters. These packets may specify a single text character, or a complete LCD line of 40 characters.

The Remote accepts real-time measurement packets that include the current U/S power, vacuum, flow rate, maximum U/S power value, maximum vacuum value, and current program state (mode). The measurement values are displayed numerically and graphically, the maximum U/S and vacuum values are used to scale the barcharts, and the program state is used to update the Event list, which is a listbox that displays all the program changes.

The Remote accepts the diagnostic dataset described above. This data is stored to a disk in a text file for later review by any Windows text editor (for example Notepad or WordPad).

PREFERRED EMBODIMENTS

Figure 1:
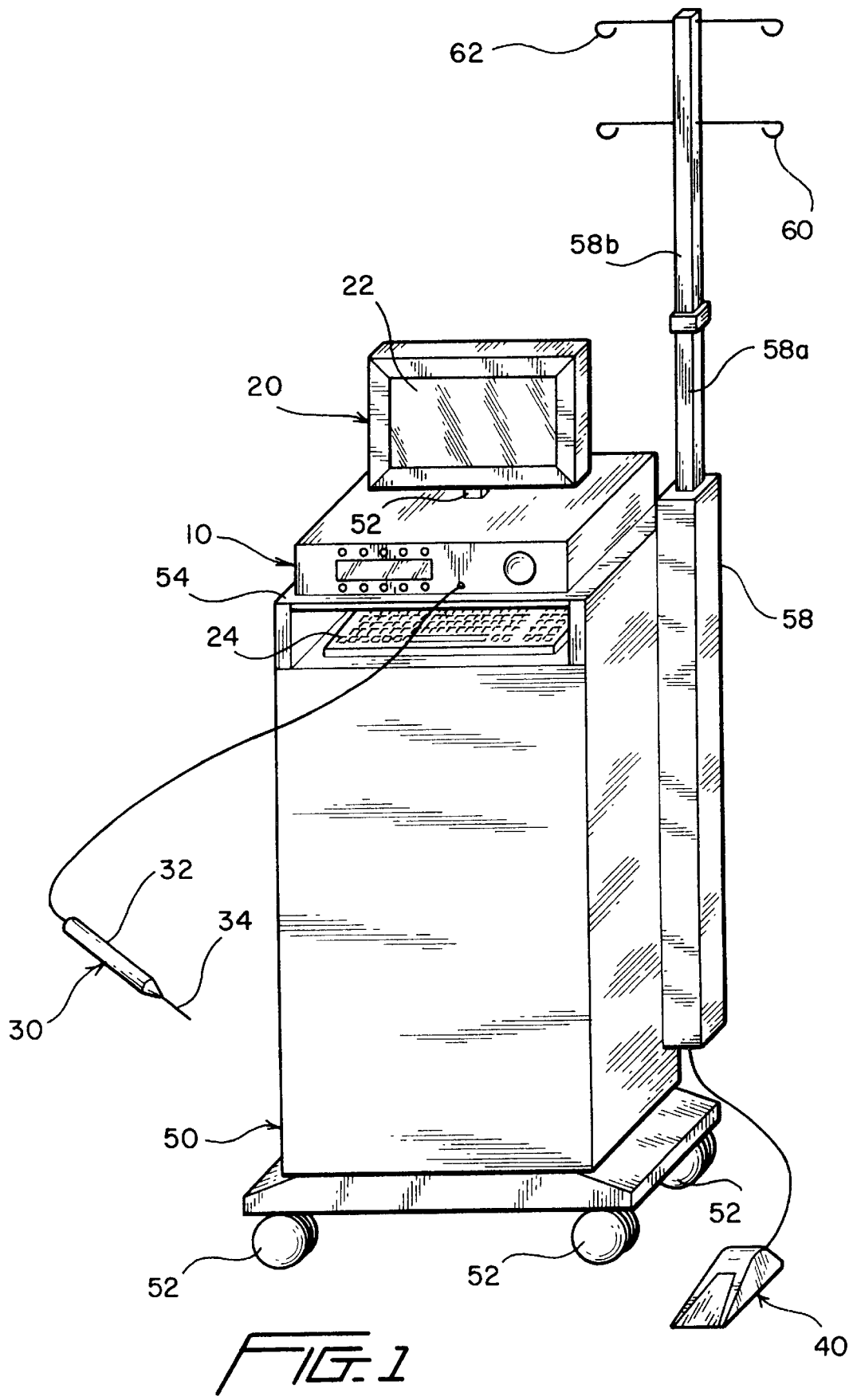
FIG. 1 is a perspective view of a phacoemulsification apparatus according to the present invention.

A particular example of an electrical surgical apparatus according to the present invention is a phacoemulsification apparatus to be described in detail below. The phacoemulsification apparatus comprises five (5) main components, including control console 10, personal computer 20, hand piece 30, foot pedal 40, and movable stand 50.

I. CONTROL CONSOLE

Figure 2:
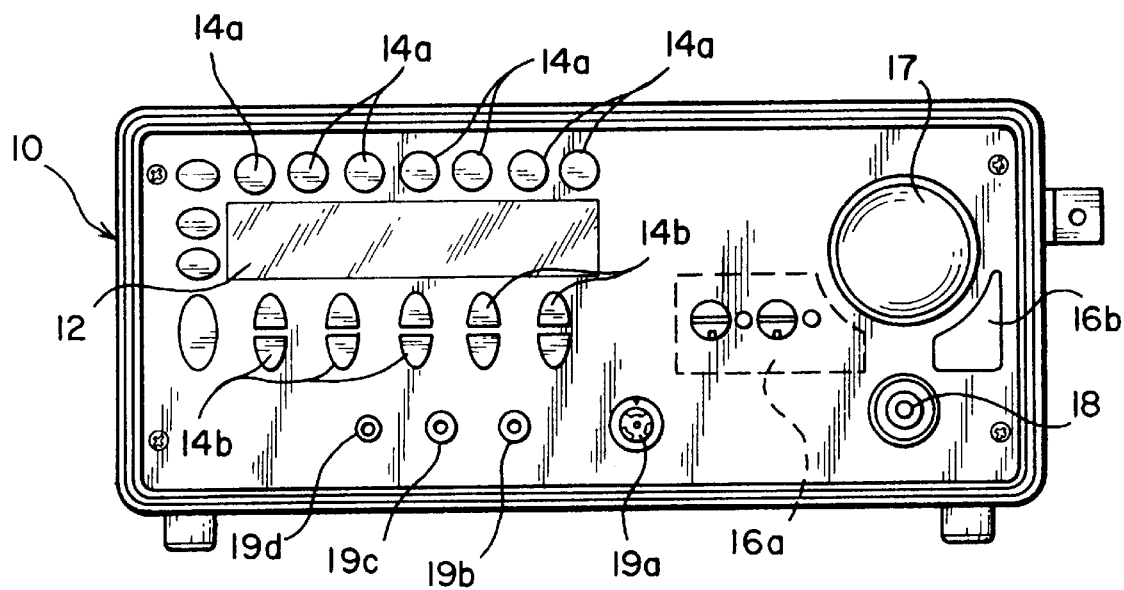
FIG. 2 is a detailed front elevational view of the control console component of the phacoemulsification apparatus shown in FIG. 1.
Figure 3:
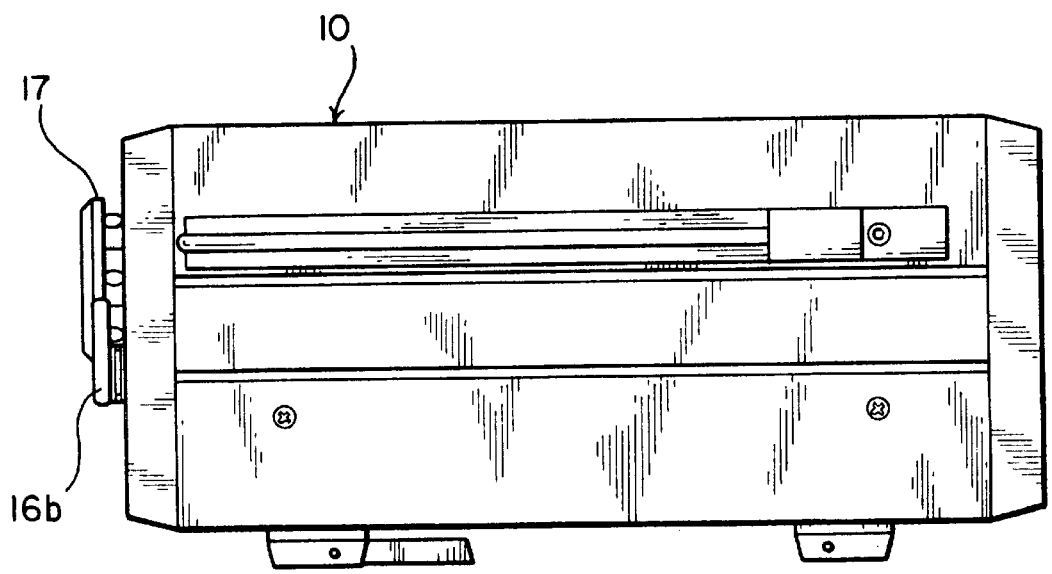
FIG. 3 is a side elevation view of the control console shown in FIG. 2.
Figure 4:
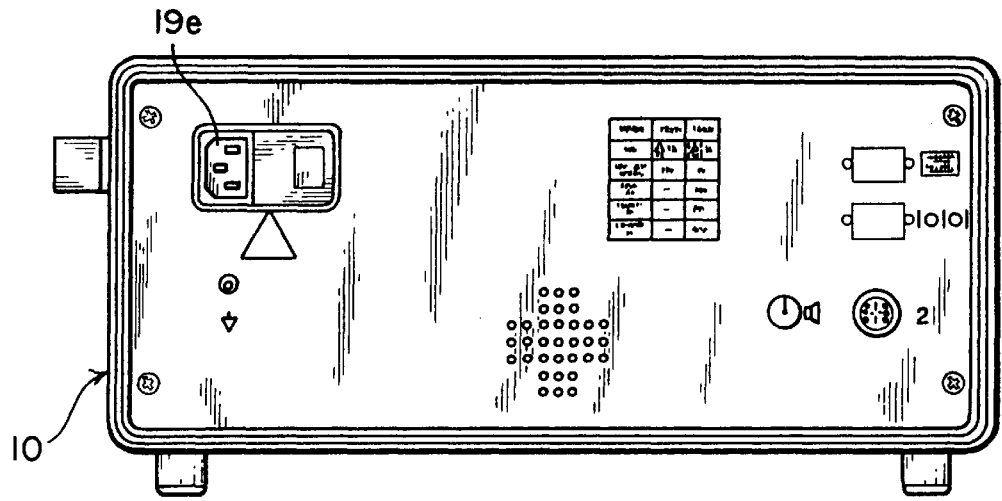
FIG. 4 is a rear elevational view of the control console shown in FIG. 2.
Figure 5:
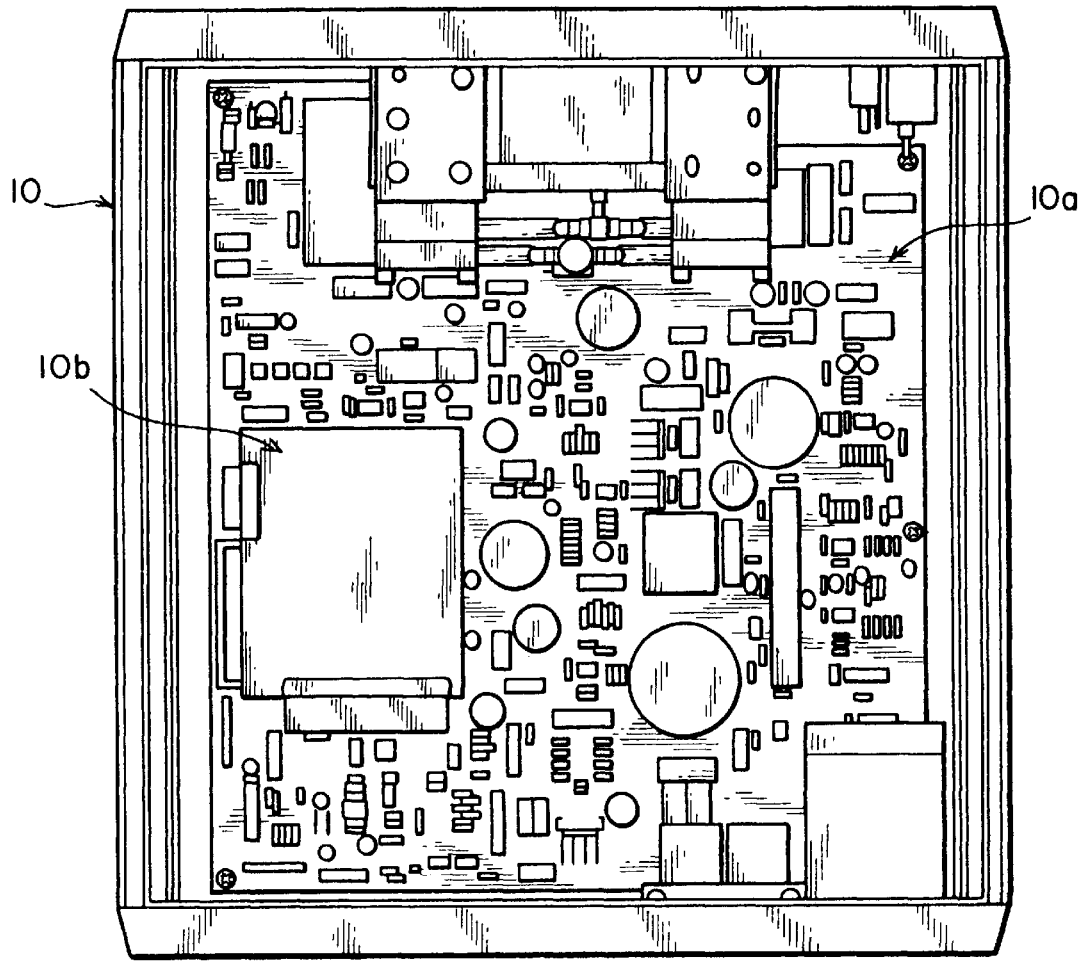
FIG. 5 is a top elevational view inside the control console shown in FIG. 2.

The control console 10 is provided with a display 12, touch control buttons 14a and 14b, removable tubing cassette 16a and stationary tubing holder 16b, peristaltic pump 17, and vacuum sensor 18 provided on a front panel thereof, as shown in FIG. 2. The front panel is also provided with an ultrasonic supply jack 19a for connecting a cable leading to the hand piece 30, and additional ports 19b, 19c and 19d. The back panel of the control console 10 is provided with a conventional AC power jack The console encloses various electrical components, including circuit board 10a and microcontroller 10b.

II. PERSONAL COMPUTER

Figure 6:
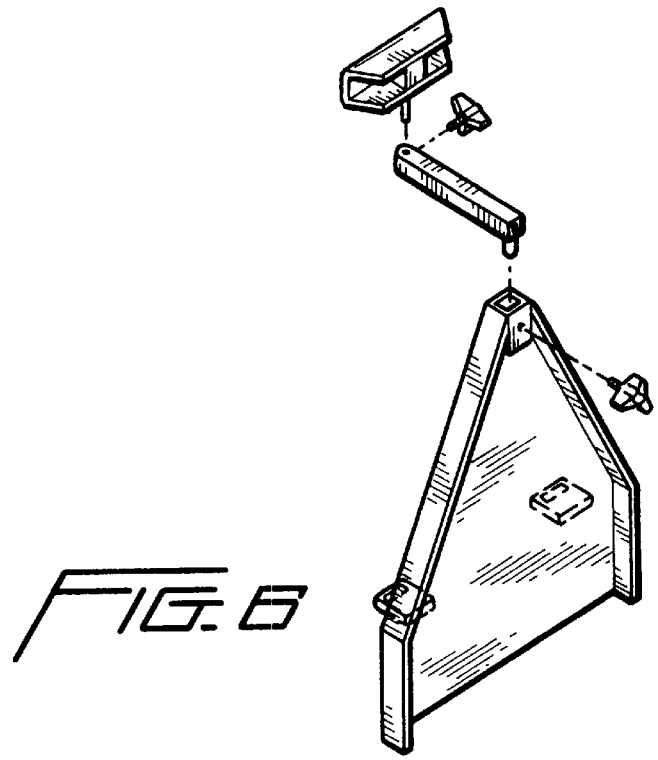
FIG. 6 is a perspective view of a movable pivot arm to be connected to the back of the stand to support the personal computer above the control console.
Figure 7:
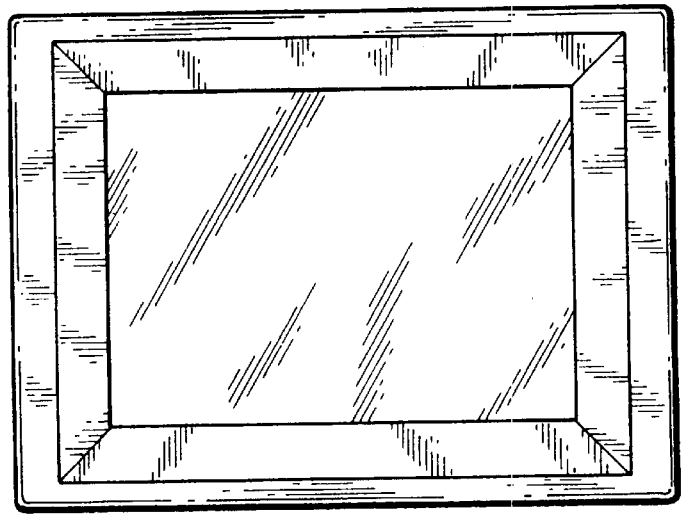
FIG. 7 is a front elevational view of the personal computer component of the phacoemulsification apparatus shown in FIG. 1.
Figure 8:
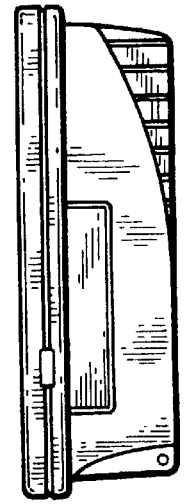
FIG. 8 is a right side elevational view of the personal computer shown in FIG. 7.
Figure 9:
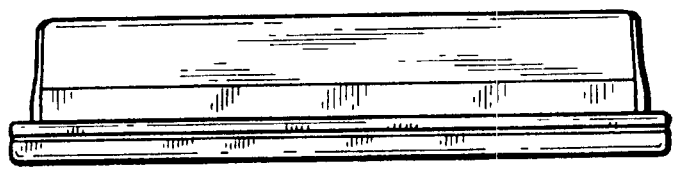
FIG. 9 is a top planar view of the personal computer shown in FIG. 7.

The personal computer 20 is provided with an integral screen 22. A keyboard 24 wired to the personal computer 20 can be provided optionally. The personal computer 20 is supported above the console 10 by a movable swing arm 42, as shown in FIG. 6, which is mounted to the back of the stand 40. The movable swing arm 42 allows a user to pivot the personal computer along a substantially vertical axis, and the movable swing arm can also be configured to provide additional axis of movement (e.g. tilting up and down, twisting, etc.).

The personal computer for use in the present invention can have various configurations. A notebook type personal computer is preferable due to its compact size. However, a personal computer 20 having the personal computer and screen integrated into a single unit is currently most preferred.

An example of a suitable personal computer for use with a phacoemulsification apparatus according to the present invention is as follows:

1) IBM AT compatible personal computer with integrated super I/O;
2) VGA card;
3) touchscreen control;
4) ethernet 10BT with an external floppy interface;
5) built in 12.1 TFT Color LCD with a MAX of 800×600 resolution;
6) Pentium MMX 233 megahertz processor with 128K cache, 32 megabytes of onboard memory;
7) 2 megabytes video memory;
8) 6 gigabytes hard disk drive;
9) one (1) PCI slot;
10) SNAZZI video capture card for the one (1) PCI slot;
11) optional external CD Rom recorder The SNAZZI video capture card is independent of the built in VGA card and provides hardware compression at 11 MB/minute. This equates roughly to 60 minutes of video on one compact disc. The quality of this capture and compression is excellent.

The system will, as an option, also support an external CD Rom recorder. This will allow the digital storage of videos captured using the SNAZZI card. The Hard Drive will be capable of storing roughly six (6) hours of video (363 minutes).

Figure 10:
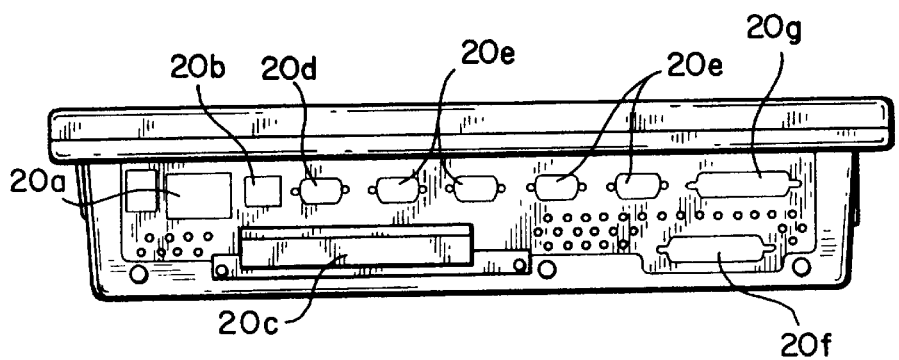
FIG. 10 is a schematic bottom view showing the external connectors and ports of the personal computer shown in FIG. 7.
Figure 11:
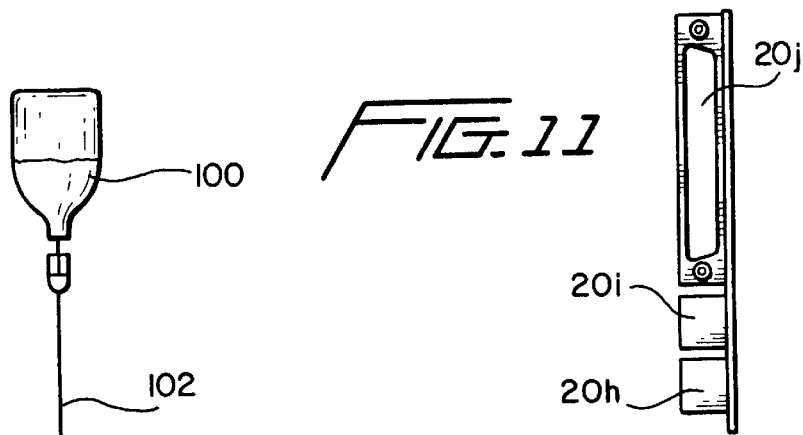
FIG. 11 is a schematic right side view showing the external connectors and ports of the personal computer shown in FIG. 7. in the phacoemulsification apparatus shown in FIG. 1.

The personal computer 20 is provided with the following I/O arrangement, as shown in FIGS. 10 and 11.

20a—AC inlet
20b—Ethernet phone jack
20c—Expansion outlet
20d—VGA port IF
20e—4×serial ports
20f—4×digital inputs/outputs
20g—Parallel port
20h—Keyboard
20i—PS/2 mouse
20j—External FDD The personal computer is preferably programmed to communicate with the control console by using a check sum approach. Specifically, the amount of bits of data being sent precedes the actual data being sent. This ensures that the data being sent from the personal computer is correct as opposed to having errors from the personal computer crashing. This packaging of information provides redundancy to allow highly reliable communication between the personal computer and control console.

The control console can also utilize voice activation hardware and/or software to allow a user to navigate through certain operations (e.g. operating mode) of the control console.

III. PHACOEMULSIFICATION HAND PIECE

The phacoemulsification hand piece 30 can be a conventional ultrasonic type hand piece including an ultrasonic transducer located within a housing 32. An ultrasonically driven needle is connected to the hand piece 30 and provided with an outer resilient sleeve (e.g. made of highly resilient silicone material).

IV. FOOT PEDAL

A conventional multi-position foot pedal can be used with the phacoemulsification apparatus according to the present invention.

V. STAND

The stand 50 is custom designed to support the other components of the phacoemulsification apparatus to facilitate easy and effective operation thereof.

The stand 50 is provided with a set of coaster wheels 52 (e.g. locking and non-locking type combinations) to allow a user to maneuver the phacoemulsification into position during an operation or later for storage.

The stand 50 is provided with an upper shelf 54 defining a top panel of the stand 50 for supporting the console 10 thereon. A lower inner shelf 56 is provided for supporting the key board 24.

The stand 50 is provided with a side support 58 including fixed telescoping portion 58a, and adjustable height telescoping portion 58b. The telescoping portion 58b is provided with a pair of irrigation bag loop supports 60 and 62 each having a pair of supporting loops. The loop supports 60 and 62 are located at different heights to provided the potential implementation of multiple irrigation bags in some system configurations (e.g. to provide variable or adjustable irrigation pressure).

VI. VENTING

Figure 12:
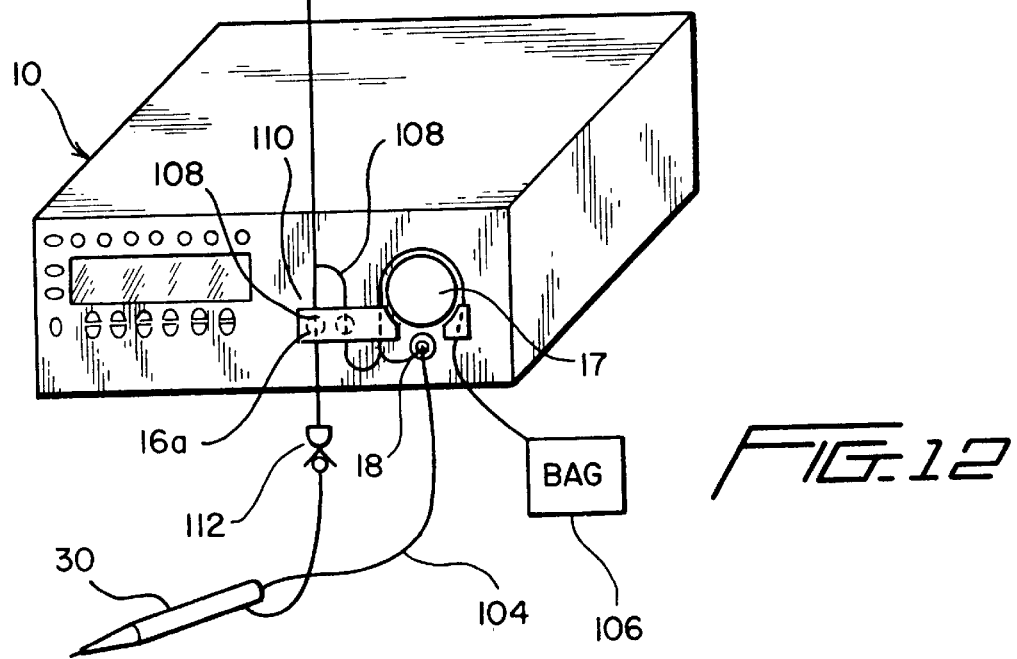
FIG. 12 is a schematic perspective view of a phacoemulsification apparatus according to the present invention.

A phacoemulsification apparatus according to the present invention shown in FIG. 12. The control console 10 is the same or similar to the control console shown in FIG. 1.

The phacoemulsification apparatus includes a single bottle or bag 100 providing a supply of irrigation solution (e.g. balanced salt solution, BSS). An infusion line 102 extends downwardly from the infusion fluid supply 100, passes through the removable cassette 16a, and connects to the hand piece 30. An aspiration line 104 is connected to the hand piece 30 and extends to the vacuum sensor 18, through the removable cassette 16a to the peristaltic pump 17 and to the disposal bag 106. A liquid bypass line connected to the infusion line 102 passes through the removable cassette and connects into the infusion line 104. The liquid bypass line 108 provides a liquid vent for equalizing the pressure between the infusion line 102 and aspiration 104 during various modes of operation.

The control console 10 is provided with two (2) solenoid valves 108 and 110 disposed behind the removable cassette 16a. The solenoid valve 108 selectively opens and closes the infusion line 102 and the solenoid valve 110 selectively opens and closes the liquid bypass line 108. Specifically, the solenoid valves 108 and 110 are remotely activated electromagnetic valves having piston portions which push outwardly from the control console 10 into back portions of the removable cassette 16a with the infusion line 102 and liquid bypass line 108 interposed therebetween. Thus, these lines are pinched open and closed depending on the control mode.

The infusion line 102 is provided with a check valve 112 to prevent the backflow of liquid from the eye when the liquid bypass line 108 is opened to provide a liquid vent to the aspiration line. It is not desirable to have liquid backflow from the eye due to contamination and potential collapse of the eye during surgery. Alternatively, the mechanical check valve 112 can be replaced with a software operated mode of operating the solenoid valves 108 and 110. Specifically, the solenoid valves 108 and 110 can be opened under a specific timed sequence (e.g. milliseconds) to prevent backflow of liquid from the eye in the infusion line 102.

Figure 13:
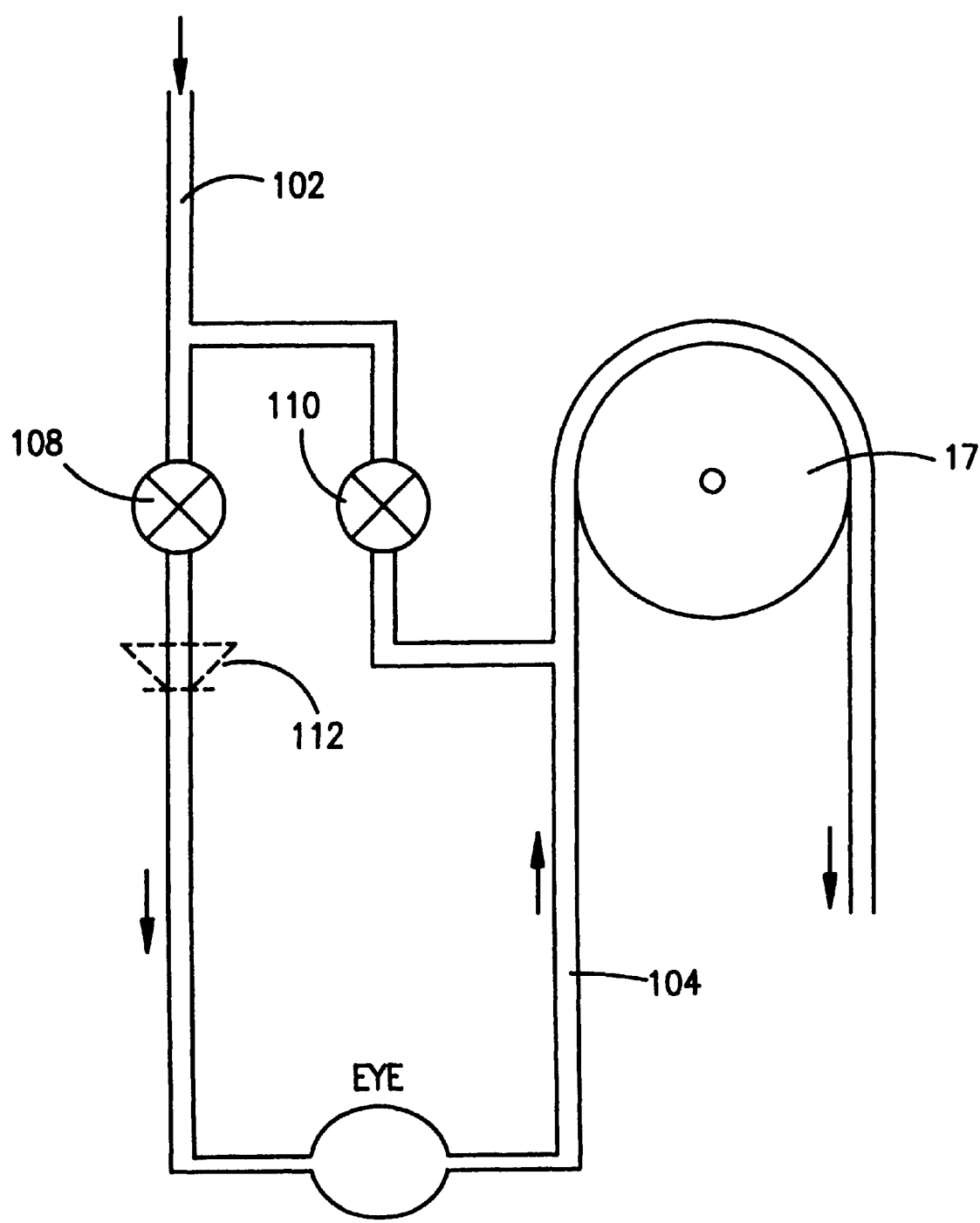
FIG. 13 is a diagrammic view of an embodiment of a liquid venting mechanism according to the present invention.

A more detailed view of an embodiment of the liquid venting mechanism for use in the phacoemulsification apparatus according to the present invention shown in FIG. 13. The following is a description of this liquid venting mechanism.

In eye surgery, fluid is brought in and aspirated out of the eye using the apparatus shown in FIG. 13. An infusion line brings fluid into the eye from a bottle located a few feet above the eye and a vacuum pump aspirates the fluid through an aspiration line. During the operation of the pump, the infusion valve is open allowing fluid to flow. This valve is usually closed when aspiration is no longer needed. In order to cancel the vacuum built in the aspiration line venting is provided through a valve which is normally closed when the pump aspirates and opens for a short period of time when the pump stops.

In a normal operation the pressure in the eye must be above the atmosphere. Otherwise, the eye will collapse. However, in the aspiration line, next to the pump the pressure will be always negative. In case of an occlusion, the pressure in the entire aspiration line will be negative.

When the vent valve opens, fluid flows from the bottle into the aspiration line killing the negative pressure. However, since the eye is also at a positive pressure, fluid will also flow out of the eye, through the infusion line until the transient regime becomes stable. Consequently, during this transition, a visible bouncing of the cornea and posterior capsule will be noticed. This bounce could damage parts of the eye.

In order to avoid this situation, existing technology utilize a check valve (figured with dotted line) installed on the infusion line to prevent back flow. However, the check valve could fail without any warning. Any failure of the check valve, in either open or close condition could produce unwanted effects to the eye.

The present invention presents a method of improving the system described in the above. Implementing the following sequence for opening and closing the infusion and vent valves during the venting process will completely eliminate the back flow.

Sequence:
1. VENT COMMAND
2. STOP THE PUMP
3. WAIT 100 MILLISECONDS
4. CLOSE THE INFUSION VALVE
5. WAIT 100 MILLISECONDS
6. OPEN THE VENT VALVE UNTIIL VACUUM DROPS TO ZERO
7. CLOSE THE VENT VA LVE
8. OPEN THE INFUSION VALVE FOR 500 MILLISECONDS
9. CLOSE THE INFUSION VALVE It can be seen that by closing the infusion valve during the vent time, back flow is prevented while the transient process takes place. This eliminates the need for using the check valve.

We claim:

1. A phacoemulsification apparatus, comprising:
   a control console;
   a phacoemulsification handpiece electrical connected to and driven by said control console; and
   a personal computer interfaced to said control console, said personal computer including a visual display, said personal computer including a disk or windows based operating system,
   wherein the phacoemulsification apparatus is configured so that said control console is operated as a master and said personal computer is operated as a slave to allow said control console to continue operating even in the event of a failure of operation of said personal computer.

2. An apparatus according to claim 1, wherein said personal computer is directly connected by hard wiring to said control console.

3. An apparatus according to claim 1, wherein said personal computer is remotely connected by hard wiring to said control console.

4. An apparatus according to claim 1, wherein said personal computer is remotely connected by a wireless communication link to the phacoemulsification apparatus.

5. An apparatus according to claim 4, wherein said wireless communication link includes a satellite link.

6. An apparatus according to claim 5, wherein said wireless communicating link includes electromagnetic wave communication.

7. An apparatus according to claim 1, wherein said personal computer is connected to said control console by an electrical cable connected to an isolated serial port of said personal computer.

8. An apparatus according to claim 1, wherein said personal computer is programmed to communicate with said control console by sending packets of data with check sums.

9. An apparatus according to claim 1, including an input device connected to said personal computer.

10. An apparatus according to claim 9, wherein said input device is a keyboard.

11. An apparatus according to claim 1, wherein said visual display is integrated with said personal computer.

12. A phacoemulsification apparatus, comprising:

a source for providing irrigation fluid to an eye;

an aspiration device for aspirating fluid from the eye;

a phacoemulsification handpiece;

a control console electrically connected to said handpiece for operating and driving said handpiece; and a windows based personal computer interfaced to said control console, wherein the phacoemulsification apparatus is configured so that said control console is operated as a master and said personal computer is operated as a slave to allow said control console to continue operating even in the event of a failure of operation of said personal computer.

\* \* \* \* \*